(12) United States Patent
Hung et al.

(10) Patent No.: US 11,149,015 B2
(45) Date of Patent: Oct. 19, 2021

(54) METHODS FOR PRODUCING TETRAHYDROFURAN

(71) Applicant: DAIREN CHEMICAL CORPORATION, Taipei (TW)

(72) Inventors: Shih-Bo Hung, Taipei (TW); Tian-Yuan Lin, Taipei (TW)

(73) Assignee: DAIREN CHEMICAL CORPORATION, Taipei (TW)

( * ) Notice: Subject to any disclaimer, the term of this patent is extended or adjusted under 35 U.S.C. 154(b) by 101 days.

(21) Appl. No.: 16/782,342

(22) Filed: Feb. 5, 2020

(65) Prior Publication Data

US 2021/0061780 A1 Mar. 4, 2021

(30) Foreign Application Priority Data

Aug. 29, 2019 (TW) .................................. 108131060

(51) Int. Cl.
*C07D 307/08* (2006.01)
*B01J 47/02* (2017.01)

(52) U.S. Cl.
CPC ............ *C07D 307/08* (2013.01); *B01J 47/02* (2013.01)

(58) Field of Classification Search
CPC ................ C07D 307/08; B01J 47/02
See application file for complete search history.

(56) References Cited

U.S. PATENT DOCUMENTS 7,935,834 B2 * 5/2011 Bhattacharyya ....... B01J 35/002
549/325
9,284,289 B2 * 3/2016 Yamashita ........... C07D 307/08

FOREIGN PATENT DOCUMENTS

| CN | 107011290 A | 8/2017 |
| TW | 201542536 A | 11/2015 |

OTHER PUBLICATIONS

Office Action for Taiwanese patent application No. 108131060 dated Aug. 24, 2020.

* cited by examiner

*Primary Examiner* — D Margaret M Seaman
(74) *Attorney, Agent, or Firm* — Kelly & Kelley, LLP

(57) ABSTRACT

The present disclosure provides a method for producing tetrahydrofuran (THF). The method includes: feeding 1,4-butanediol into a reactive distillation apparatus; performing the dehydration reaction in the presence of an acidic catalyst; and producing the top stream containing product THF and the bottom stream from the reactive distillation apparatus, wherein a weight ratio of a water content in the bottom stream to a water content in the top stream is 0.05 to 2.4, thereby providing a high conversion rate and more cost-effectiveness, and enhancing the value of the industrial application.

20 Claims, 3 Drawing Sheets

METHODS FOR PRODUCING TETRAHYDROFURAN

1. TECHNICAL FIELD

The present disclosure relates to methods for producing tetrahydrofuran, and more particularly, to a method for producing tetrahydrofuran from a mixture containing 1,4-butanediol in a reactive distillation apparatus.

2. DESCRIPTION OF ASSOCIATED ART

Tetrahydrofuran (THF) is commonly used as an organic solvent in industry and a raw material in chemical engineering, the uses of which encompass the fields of macromolecules, pharmaceuticals and other organic synthesis, adhesives, surface treatments, paintings, precise electronics, electroplating, and the like.

The current industrial methods for producing THF include: a hydrogenation process of maleic anhydride, a dichlorobutene process, an oxidation process of butadiene and a dehydration process of 1,4-butanediol (BDO), among these, the dehydration process of 1,4-butanediol is performed by subjecting 1,4-butanediol to a dehydration reaction in a presence of an acidic catalyst to produce THF, and has the advantages of simple route, mature technique, low reaction temperature and high yield when compared to other processes.

The common continuous process for producing THF uses a fix bed reactor packed with a solid catalyst to perform catalytic reaction of liquid reactants. However, this process is limited by the chemical equilibrium, and therefore, it leads to a low conversion level (with the conversion rate generally from 35% to 45%) and a low product yield. As such, there is a need to recycle a large amount of unreacted 1,4-butanediol, such that cause high operating cost.

Currently, a reactive distillation technique has been applied for continuous production. In this technique, both reaction and separation procedure are performed in a single unit, and accordingly, the product will be removed from the reactant continuously to overcome the limitation of reaction equilibrium, therefore, a higher conversion rate and a compact process can be achieved.

However, when practically use reactive distillation technique for producing THF through a dehydration process of 1,4-butanediol, the operation of reactive distillation apparatus, the amount of catalyst loading or the amount of the water byproduct has a strong impact on the conversion of 1,4-butanediol. The liquid phase reactant stream cannot be in contact sufficiently with the catalyst when operating at improper reflux ratio or a condition of too large weight hourly space velocity (WHSV) value, it is still difficult to achieve a high conversion rate through a single reactive distillation apparatus. To increasing the conversion of 1,4-butanediol, it is generally necessary to add pre-reactors at the upstream of the reactive distillation column, or to recycle a part of 1,4-butanediol stream, which result more cost for equipment.

In view of the foregoing, it is necessary to propose a method for producing THF with a high conversion rate and a low cost to solve the problems existing in the conventional techniques described above.

SUMMARY

In order to solve the problems mentioned above, the present disclosure provides a method for producing THF, which includes performing the dehydration reaction of a reactant stream containing 1,4-butanediol in a reactive distillation apparatus, while controlling a weight ratio of a water content in the bottom stream to a water content in the top stream to increase the conversion rate of the reactant stream.

Specifically, a method for producing THF includes: feeding a reactant stream containing 1,4-butanediol into a reactive distillation apparatus, and performing the dehydration reaction in a presence of an acidic catalyst to produce the top stream containing THF and the bottom stream from the reactive distillation apparatus, wherein a weight ratio of a water content in the bottom stream to a water content in the top stream is from 0.05 to 2.4.

In an embodiment, the reflux ratio at the top of the reactive distillation apparatus is from 0.1 to 1.0.

In an embodiment, the reactive distillation apparatus includes, from top to bottom, a rectification section and a reactive section, wherein the reactive section is packed with an acidic catalyst. In another embodiment, the reactive section includes a plurality of plates, in each of which a plurality of catalyst packing zones for packing the acidic catalyst are arranged.

In still another embodiment, the acidic solid catalyst is an ion-exchange resin, wherein the ion-exchange resin has a total concentration of acid sites of from 1.3 to 2.0 eq/L of wet resin, a specific surface area of from 20 to 50 $m^2/g$, and an average pore size of from 30 to 70 nm.

In an embodiment, the WHSV of the reactant stream containing 1,4-butanediol is from 2.1 to 2.5 $hr^{-1}$.

In another embodiment, the reactant stream containing 1,4-butanediol is fed into the uppermost plate in the reactive section of the reactive distillation apparatus, i.e., the first plate described herein.

In another embodiment, the plate number is from 10 to 20 in the rectification section, and is from 40 to 60 in the reactive section, wherein the temperature is from 79 to 101° C. at the rectification section and is from 90 to 120° C. at the reactive section, and the pressure in the reactive section is from 0.8 to 1.0 $kg/cm^2G$.

In another embodiment, a water content is from 1.6 to 13 wt % at the uppermost plate, and is from 67 to 94 wt % at the lowermost plate in the reactive section.

In an embodiment, the acidic solid catalyst is an ion-exchange resin, and the weight hourly space velocity of the reactant stream containing 1,4-butanediol is from 2.1 to 2.5 $hr^{-1}$.

In an embodiment, the bottom of the reactive distillation apparatus is connected to a reboiler, so that a portion of the reactant stream is vaporized to a vapor stream, which is in counter-current contact with the reactant stream containing 1,4-butanediol falling down in a liquid state. In an embodiment, the temperature of the reboiler is 115 to 130° C.

In an embodiment, the liquid viscosity at the bottom of the reactive distillation apparatus is less than 0.6 cp.

The present disclosure further provides a method for producing THF, which includes: feeding a reactant stream containing 1,4-butanediol into a reactive distillation apparatus containing, from top to bottom, a rectification section and a reactive section packed with an acidic catalyst, and subjecting 1,4-butanediol to a dehydration reaction in a presence of the acidic catalyst to produce a top stream containing THF and a bottom stream from the reactive distillation apparatus, wherein the temperature of the reactive section is 90 to 120° C., and the reactant stream containing 1,4-butanediol is controlled at a WHSV of 2.1 to 2.5 hr$^{-1}$, so that the weight ratio of a water content in the bottom stream to a water content in the top stream is from 0.05 to 2.4.

According to the method of the present disclosure, by controlling the ratio of the water content in the bottom stream to the water content in the top stream, the reaction zone of the reactive distillation apparatus is maintained under a preferable condition to significantly enhance the conversion rate of the reactant stream and to reduce equipment cost, so that the process for producing THF has more economic benefits and values for industrial applications.

BRIEF DESCRIPTION OF THE DRAWINGS

The implementing modes of the present disclosure will be described by references to the appended exemplary drawings.

DETAILED DESCRIPTION OF THE EMBODIMENTS

Figure 1:
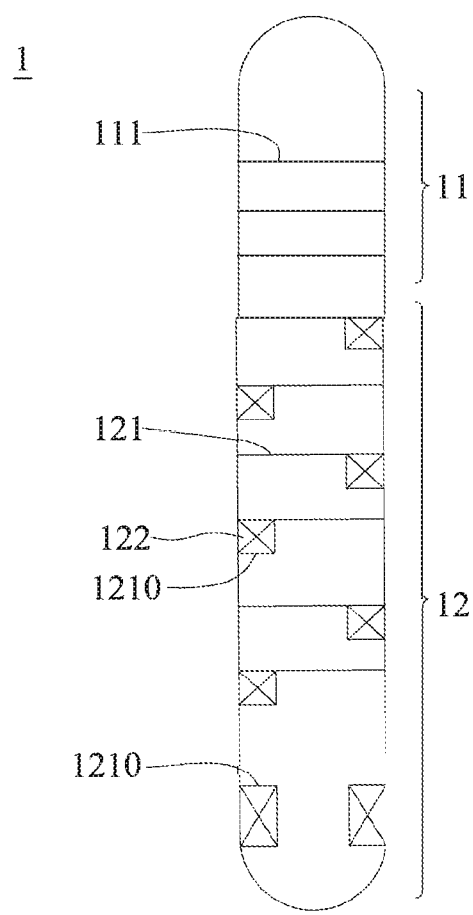
FIG. 1 is a schematic diagram showing the structure of a reactive distillation apparatus of the present disclosure.

The following specific embodiments are used to illustrate the detailed description of the present disclosure, such that a person skilled in the art may readily conceive the advantages and effects of the present disclosure from the disclosure of the present specification. The present disclosure may also be implemented or applied by other different ways of implementation. Each of the details in the present specification may be modified and altered in any way based on different aspects and applications, without departing from the spirit of the present disclosure.

The structures, proportions, sizes, etc. illustrated in the figures appended to the present specification are all merely used for coping with the content of disclosure of the present specification, so as to enhance the understanding and perusal of one skilled in the art. They are not used to limit the implemental limitations of the present disclosure, such that they lack substantial technical meanings. Without affecting the effect brought about and the goals to be achieved by the present disclosure, any modification of a structure, alteration of a proportion or adjustment of a size should still fall within the scope of the technical content disclosed in the present disclosure. At the same time, terms, such as "above," "below," "top," "first," "second," "one," etc. used in the present specification, are merely for the clarity of the descriptions, rather than limit the implemental scope of the present disclosure. Without substantially altering the technical content, an alteration or adjustment of relative positioning can also be regarded as an implemental scope of the present disclosure.

According to the present disclosure, a method for producing THF is provided, which includes: feeding a reactant stream containing 1,4-butanediol into a reactive distillation apparatus, and performing the dehydration reaction in a presence of acidic catalyst to produce the top stream containing THF and bottom stream from the reactive distillation apparatus, wherein a weight ratio of a water content in the bottom stream to a water content in the top stream is from 0.05 to 2.4.

The expression "reactant stream containing 1,4-butanediol" refers to a reactant stream including 1,4-butanediol as its main component and containing a small amount of impurities, wherein the 1,4-butanediol can be prepared by any known method, e.g., by hydrogenation of maleic anhydride, by Reppe process from acetylene, by oxidation of propylene, by a fermentation method, and by diacetoxylation, hydrogenation and hydrolysis of butadiene, without specific limitation; and the impurities are byproducts from the well-known processes described above, such as 2,4-hydroxybutoxytetrahydrofuran (BGTF), 1-acetoxy-4-hydroxybutane, dehydrated dimer and trimer of 1,4-butanediol, and γ-butyrolactone. In an embodiment, the reactant stream includes 95 wt % or more of 1,4-butanediol, or can be the one containing 99 wt % or more of or pure 1,4-butanediol after purification.

In the producing method of the present disclosure, a preheating treatment can be done on the reactant stream containing 1,4-butanediol before feeding it into the reactive distillation apparatus to further reduce the energy consumption of the reboiler. In fact, the reaction in the reactive distillation apparatus is still performed without any pre-reaction or preheating treatment.

The reactive distillation apparatus refers to a reaction vessel combined with a distillation unit, the role of which is separating the reactants and products during reaction to overcome the limitation of reaction equilibrium, and thus to achieve a high conversion of the reaction. In one embodiment, the reactive distillation apparatus includes at least a rectification section and a reactive section; and in other embodiments also can include, from top to bottom, a rectification section, a reactive section and a stripping section, wherein there is no restriction on the form of the reaction vessel or the flowing mode of the fluid in the apparatus. In the method of the present disclosure, the product THF is discharged from the top of the reactive distillation apparatus.

The rectification section is to provide sufficient gas-liquid contact and to achieve the propose of separating and purifying THF by the difference in volatilities between components of the mixture and the difference of distribution of vapor-liquid fraction, wherein there is no restriction on the form of the rectification section. In a particular embodiment, the structure of the rectification section can be selected from structured packing, a random packing, or plates. Among these, the structure of the rectification section in the form of plates is particularly preferable, with the plate number being from 10 to 20.

In other embodiments, the rectification section can have a plate number of 11, 12, 13, 14, 15, 16, 17, 18 or 19, but not limited thereto.

In a particular embodiment, the temperature of the rectification section is from 79 to 101° C. In other embodiments, the temperature of the rectification section can be 79.5, 79.7, 80, 80.5, 81, 81.4, 81.6, 82, 83, 84, 84.7, 85, 86, 87, 87.7, 88, 89, 90, 91, 91.5, 92, 93, 94, 95, 96, 96.1, 96.6, 97, 97.9, 98, 99, 99.4, 99.6, 100, 100.1, 100.4 or 100.6° C., but not limited thereto.

The reactive section includes an acidic catalyst, and provides sufficient contact of the reactant stream and the acidic catalyst, so as to achieve fast reaction. The acidic catalyst can be in a form of solid or liquid, with an acidic solid catalyst being particularly preferable.

Since the residence time of reactant stream in reactive section will do effect, the conversion rates of the catalytic reaction can be controlled through the structure of the reactive section, the packing form of the catalyst, and the weight ratio between the catalyst and the reactant stream. In a particular embodiment, the reactive section can be selected to have a structure containing a plurality of plates capable of holding the acidic solid catalyst, and the plate number is from 40 to 60. The plates capable of holding the acidic solid catalyst is described in U.S. Pat. No. 7,909,966 B2, which is incorporated herein by reference in its entirety. Through the arrangement of the plurality of plates capable of holding the acidic solid catalyst such as 40 to 60 plates, the residence time of the reactant stream is extended, and the conversion rate of the reaction is increased.

In other embodiments, the reactive section can have a plate number of 41, 42, 43, 44, 45, 46, 47, 48, 49, 50, 51, 52, 53, 54, 55, 56, 57, 58 or 59, but not limited thereto.

In an embodiment, the acidic solid catalyst is installed at bottom sump of the reactive distillation apparatus, where no plate is present, and on all plates of the reactive section. The bottom sump of the reactive distillation apparatus where no plate is present is provided much higher volume for acidic solid catalyst packing installed than that on the plates of the reactive section, which gives the maximum packing quantity of the acidic solid catalyst to enhance the yield of the process.

In a particular embodiment, the plurality of plates capable of holding the acidic solid catalyst is packed with the acidic catalyst in a mode selected from a fix box, a screen pack, and a similar structure.

In still another particular embodiment, the weight hourly space velocity of the reactant stream containing 1,4-butanediol is 2.1 to 2.5 $hr^{-1}$. In other embodiments, the weight hourly space velocity of the reactant stream containing 1,4-butanediol can be 2.13, 2.15, 2.16, 2.27, 2.34, 2.39, 2.43 or 2.47 $hr^{-1}$, but not limited thereto.

As the dehydration of 1,4-butanediol is performed in the presence of an acidic catalyst with a higher activity, controlling the reaction temperature is particularly important. In a particular embodiment, the temperature of the reactive section is from 90 to 120° C. The acid group tends to desorb from the acidic catalyst to result in degradation of the catalyst, if the reaction temperature is too high; and a lower reaction rate will occur to result in a relatively poor yield, if the reaction temperature is too low.

In other embodiments, the temperature of the reactive section can be 91, 92, 93, 94, 95, 96, 97, 98, 99, 100, 101, 102, 103, 104, 105, 106, 107, 108, 109, 110, 111, 112, 113, 114, 115, 116, 117, 118, 119° C.

In another particular embodiment, the pressure of the reactive section is 0.8 to 1.0 $kg/cm^2G$. In other embodiments, the pressure of the reactive section can be 0.83, 0.86, 0.9, 0.93 or 0.96 $kg/cm^2G$, but not limited thereto.

In addition, the stripping section has a structure and follows a principle both being the same as the rectification section, however, the stripping section is for the purpose of separating the composition containing those with high boiling points, including impurities, byproducts and unreacted 1,4-butanediol. In a particular embodiment, the stripping section has a structure containing a plurality of plates, and the plate number is from 2 to 5.

The reactant stream can be fed at the upper, the middle or the lower portion of the reactive section. In a particular embodiment, the reactant stream containing 1,4-butanediol is fed at the upper portion of the reactive section. More specifically, the reactant stream containing 1,4-butanediol is fed at the uppermost plate in the reactive section of the reactive distillation apparatus, i.e., the first plate described herein.

The acidic solid catalyst described above can be selected from a mineral-supported catalyst, a solid resin type of catalyst, and a solid acidic catalyst pretreated with phosphoric acid or sulfuric acid.

The mineral-supported catalyst includes the solid oxide of at least one element of Groups 4, 6, 13 and 14 in the Periodic Table, such as titanium dioxide, zirconium oxide, zirconium dioxide, aluminum oxide, γ-silica or tin oxide, and the solid oxide incorporated with a plurality of above elements, such as zeolite, montmorillonite or molecular sieves.

The solid resin types of catalyst can be selected from ion-exchange resins such as Amberlyst series (produced by Dow Chemical), Purolite series (produced by Purolite) and DIAION SK series (produced by Mitsubishi Chemical) products, as well as fluorosulfonic acid-containing resins such as Nafion products (produced by Dupont); wherein the ion-exchange resins are preferably acidic ion-exchange resins. In a particular embodiment, the ion-exchange resin in an aqueous state has a total concentration of acid sites of from 1.3 to 2.0 eq/L. In other embodiments, the ion-exchange resin in an aqueous state can have a total concentration of acid sites of 1.4, 1.5, 1.6, 1.7, 1.8 or 1.9 eq/L.

The ion-exchange resin can be applied to catalyze a reaction at a higher efficiency, since it has a higher specific surface area and more active sites due to its nanometer-scaled porous structure, with the ion-exchange resin having an average pore size of 30 to 70 nm or the ion-exchange resin having a specific area of 20 to 50 $m^2/g$ being particularly preferable. In other embodiments, the ion-exchange resin can have an average pore size of 40, 45, 50, 55, 60 or 65 nm and a specific surface area of 25, 30, 35, 40 or 45 $m^2/g$.

In another particular embodiment, the solid resin type catalyst can be optionally modified with a soluble material in its structure, and the soluble material is immediately released upon contacting the reactant stream to prevent the formation of byproducts, wherein the soluble material for modification can be an organic compound selected from amines and amides.

In addition to the design of the reactive distillation apparatus and the selection of the acidic solid catalyst, water is an important key for effective production of THF. The presence of water is adverse to progress of the overall reaction. However, byproducts such as dimers, trimers and oligomers (with a molecular weight of from 200 to 1,000) formed by intermolecular dehydration of 1,4-butanediol, or acetal polymers formed by 1,4-butanediol and impurity in the reactant stream can be partial dissolved in water.

Therefore, the presence of water can reduce the influence on the process stability caused by fouling, further decrease liquid viscosity in the reactive distillation apparatus efficiently, increase heat transfer efficiency, and reduce energy consumption. However, water is adverse to the dehydration reaction, and there is still a problem of decreasing conversion rate of the reactant stream simply by controlling the water content in the reactive distillation apparatus (although the water content present in the reactive distillation apparatus is one condition of concern in the art).

To solve the problems, the water content in the stream discharged from the reactive distillation apparatus is controlled in the present disclosure. In the method of the present disclosure, the weight ratio of the water content of the bottom stream to the water content of the top stream is controlled in the range of from 0.05 to 2.4, thereby keeping distribution of the vapor-liquid fraction in the reactive distillation apparatus at the optimal state. Therefore, the process for producing THF is more economically advantageous.

In other embodiments, the weight ratio of the water content of the bottom stream to the water content of the top stream can be 0.08, 0.1, 0.16, 0.2, 0.5, 0.7, 0.9, 1.3, 1.5, 1.7, 1.9 or 2.2, but not limited thereto.

In a particular embodiment, the flow rate of the top stream is from 10 to 17 metric tons/hour (MT/hr), and the water content of the top stream ranges from 7 wt % to 20 wt %. In another particular embodiment, the flow rate of the bottom stream is from 0.5 to 6 metric tons/hour (MT/hr), and the water content of the bottom stream ranges from 23 wt % to 72 wt %.

Controlling the ratio of the water contents between the streams discharged from the bottom and the top discharging of the reactive distillation apparatus can also include controlling the reflux ratio at the top of the reactive distillation apparatus. In a particular embodiment, the reflux ratio at the top of the reactive distillation apparatus is from 0.1 to 1.0.

In other embodiments, the reflux ratio at the top of the reactive distillation apparatus can be 0.15, 0.19, 0.195, 0.2, 0.23, 0.3, 0.35, 0.4, 0.45, 0.5, 0.55, 0.6, 0.65, 0.7, 0.75, 0.8, 0.85, 0.9, 0.95 or 1.0, but not limited thereto.

If the ratio of the water content of the bottom stream to the water content of the top stream of the reactive distillation apparatus or the reflux ratio is too low, the concentration of byproducts will be high enough to increase the liquid viscosity at the bottom of the reactive distillation apparatus, resulting in fouling of the apparatus and adverse effect on heat transfer efficiency of the reactive distillation apparatus. In contrast, if the ratio of the water content of the bottom stream to the water content of the top stream of the reactive distillation apparatus or the reflux ratio is too high, the progress of reaction will be affected adversely, resulting in reduced conversion rate.

By controlling the water content as described in examples of the present disclosure, problems of the process resulted from poor conversion rate of the reaction and precipitation of byproducts can be solved effectively, the liquid viscosity at the bottom of reactive distillation apparatus is maintained less than 0.6 cp, and therefore, the stability of the continuous process operation is enhanced effectively and a good heat transfer efficiency.

In other embodiments, the liquid viscosity at the bottom of the reactive distillation apparatus can be less than 0.513, 0.51, 0.47, 0.43, 0.429, 0.423, 0.38, 0.345, 0.33, 0.325, 0.30, 0.279, 0.27 or 0.267 cp, or alternatively can be low to 0.26 cp.

On other hand, since the water in the reactive distillation apparatus is from the dehydration described above, the temperature, the pressure and the catalyst configuration affect the amount of water formation. In a particular embodiment of the present disclosure, the temperature of the reactive section is 90 to 120° C., and the pressure of the reactive section is 0.8 to 1.0 kg/cm$^2$G. In still another particular embodiment, the weight hourly space velocity of the reactant stream containing 1,4-butanediol is from 2.15 to 2.43 hr$^{-1}$ when the reactive section utilizes an ion-exchange resin as the catalyst.

Further, the water contents at different positions in the reactive section alter in vapor-liquid fraction, in response to different temperature and pressure states. In the producing method of the present disclosure, the liquid water content is from 1.6 to 13 wt % at the uppermost plate, and is from 67 to 94 wt % at the lowermost plate in the reactive section.

In other embodiments, the water content at the uppermost plate in the reactive section can be 1.63, 5, 8, 8.27, 8.34, 8.67, 9, 10, 10.5, 10.65, 10.9, 11, 12, 12.17, 12.5 or 12.81 wt %; and the water content at the lowermost plate in the reactive section can be 67.46, 67.5, 70, 75, 80, 85, 89, 89.1, 90, 92, 92.5, 92.53, 92.86, 93, 93.1 or 93.23 wt %.

A reboiler is arranged at the bottom of the reactive distillation apparatus, and is utilized to heat the reactant stream containing 1,4-butanediol to the temperature of bubble point, thereby vaporizing a part of the reactant stream containing 1,4-butanediol to form a vapor stream which will be in counter-current contact with the liquid reactant stream containing 1,4-butanediol flowing downwards in the reactive distillation apparatus. The reboiler can be in any form known in the art, such as shell-and-tube, pipes, thermosiphon, thin film evaporation, jacket heating kettle, coil heating kettle, forced circulation, fuel fire furnace, plate type and the like. In a particular embodiment, in order to carry out the counter-current contact aforementioned, the reboiler is set at a temperature of 115 to 130° C., such that the production of THF is performed preferably with the benefits of high conversion rate, low energy consumption and low cost, and the problems such as degradation of the catalyst due to high temperature are avoided.

In other embodiments, the reboiler can be set at a temperature of 117, 119, 119.4, 119.5, 119.7, 119.9, 120, 122, 122.8, 123, 123.6, 127, 127.1 or 128° C., but not limited thereto.

If the temperature of the reboiler is too high, the acidic catalyst near the bottom of column tends to degradation. If the reaction temperature is too low, vapor stream flowing upwards cannot be generated sufficiently, causing the liquid stream will flow downwards directly via the sieve for gas passing through, resulting in the so-called "weeping" phenomenon. As such, the degree of contact between the gas phase and the liquid phase on the plates will be affected.

A condenser arranged at the top of reactive distillation apparatus is used for receiving the top stream from the reactive distillation apparatus and cooling the vapor to its dew point temperature, to generate a liquid which is returned to form counter-current contact with the vapor stream flowing upwards. The condenser can be any device known in the art, for example, a shell-and-tube type, a plate type, a direct contact type and the like. In a particular embodiment, the condenser is set at a temperature of from 40 to 75° C.

In another particular embodiment, a plurality of distillation columns can be further added downstream of the reactive distillation apparatus to concentrate the 1,4-butanediol with high purity, if the unreacted 1,4-butanediol is required to be recovered from the bottom stream.

In order to allow one skilled in the art to realize the apparatus and system for producing THF of the present disclosure, drawings are provided to describe the features and functions of the embodiments of the present disclosure in detail as following for complete understanding, but it must be noticed that the content described should not be considered as a limiting the present disclosure.

Referring to FIG. 1, a schematic diagram of a particular embodiment of the reactive distillation apparatus of the present disclosure is shown. The reactive distillation apparatus is a reactive distillation column 1 which includes: a rectification section 11 and a reactive section 12, wherein the rectification section 11 includes a plurality of plates 111; and the reactive section 12 includes a plurality of plates 121, in each of which is arranged an acidic catalyst 122 (as shown in FIG. 2) in a container 1210, such as a catalyst box, wherein the container 1210 with a larger volume is arranged at the bottom sump of the reactive distillation apparatus where no plate is arranged, and the acidic solid catalyst placed therein is configured at an amount higher than the acidic solid catalyst on each of the plates 121.

Figure 2:
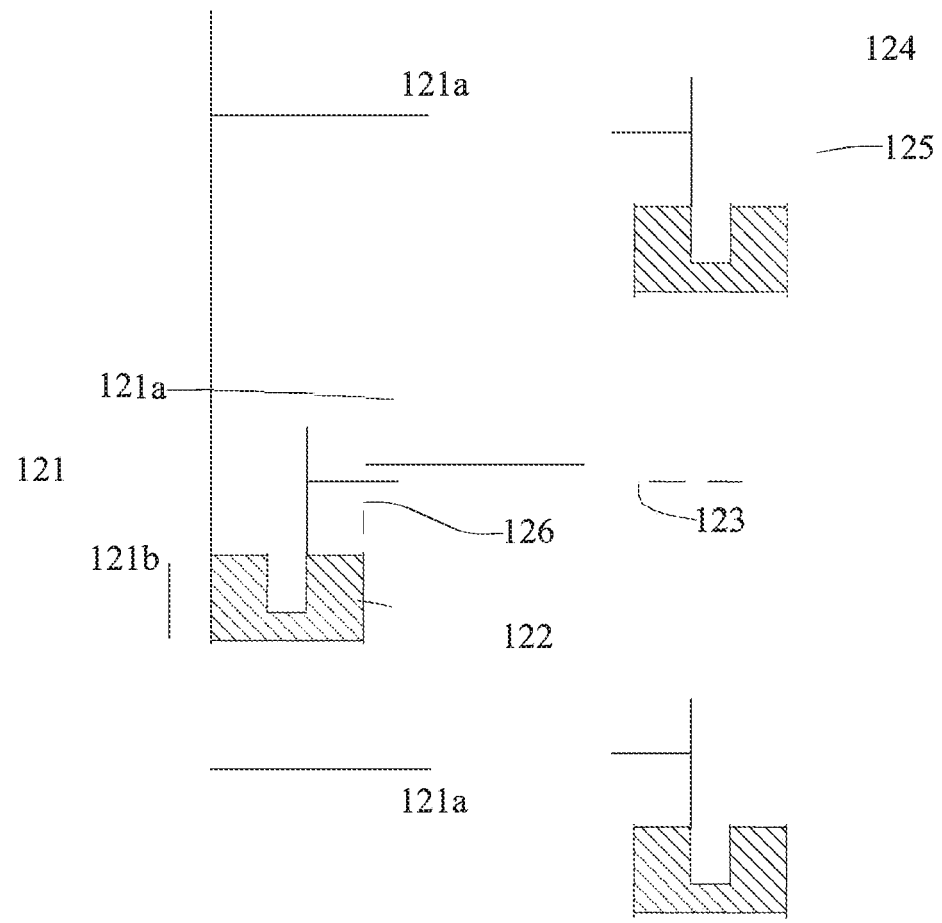
FIG. 2 is a schematic diagram showing the partial structure of the reactive section of the reactive distillation apparatus of the present disclosure.

The schematic diagram of the reactive section of the reactive distillation apparatus is further illustrated in FIG. 2. Each of the plates 121 in the reactive section 12 includes: a distillation zone 121a and a catalyst packing zone 121b equipped with the container 1210 of FIG. 1, wherein the catalyst packing zone 121b is packed with the acidic catalyst 122, and the distillation zone 121a of the plate 121 in the reactive section includes a plurality of sieve pores 123 for gas passing through. Meanwhile, the liquid reactants induced downwards from the upper plates reside in the distillation zone 121a to allow the liquid phase to be in contact with the vapor phase, until the liquid level is higher than the height of the outlet weir 124 arranged on the plate 121 in the catalyst packing zone 121b, then the liquid phase is induced into the catalyst packing zone 121b through a downcomer 125 connected to the outlet weir 124 to uniformly disperse the reactants in the catalyst packing zone 121b where the reactants are subjected to a dehydration in the presence of the acidic catalyst 122. Thereafter, the stream finally flows downwards through an overflow window 126 in the catalyst packing zone to the distillation zone 121a of the lower plate and to another catalyst packing zone 121b, which is in a stagger arrangement with the upper catalyst packing zone 121b. That is, the plates 121 in the reactive section 12 provide effects of separating and catalyzing at the same time.

The distillation zones of plates in the rectification section and the reactive section can be chosen from different types, based on their actual requirements, for example, bubble-cap plates, sieve plates, floating valve plates, jet plates, and the like.

By arrangement of the catalyst packing zones 121b, the present disclosure provides a longer residence time of the reactants and the acidic catalyst. Secondly, the effects of mixing and dispersing the reactants can be achieved by floating the acidic catalyst due to the energy generated from flowing of the liquid reactants, so that the reaction is more effectively and results in higher conversion rates. The active site of the acidic catalyst is prevented from fouling by precipitation of the byproducts due to the acidic catalyst can be floated, which is helpful to prolong the lifespan of the acidic catalyst to make the process more stable.

Figure 3:
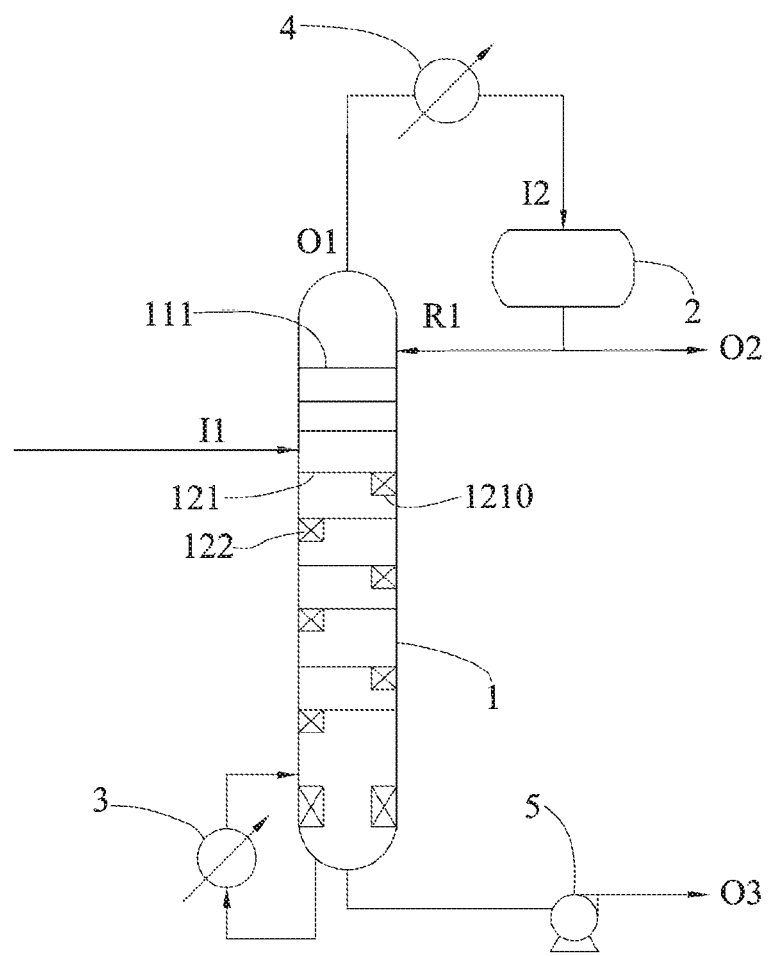
FIG. 3 is a schematic diagram showing the system for producing THF of the present disclosure.

Referring to FIG. 3, a schematic diagram of a system for producing THF of the present disclosure is illustrated. The system includes a reactive distillation column 1, a reflux drum 2, a reboiler 3, a condenser 4 and a liquid pump 5. In addition, the system includes pipelines as represented by solid lines in the figure for connecting and liquid communicating the units of the system.

In the method of the present disclosure, a reactant stream containing 1,4-butanediol is fed into the reactive distillation column 1 from an inlet I1 at the position of the first plate in the reactive section, and the reactant stream is subjected to dehydration gradually in the catalyst packing zone on each of the plates 121 of the reactive section and to mass transfer and heat transfer in the distillation zones. After flowing to the bottom of the reactive distillation column, the liquid stream is heated, vaporized and returned through the reboiler 3 to provide a vapor stream. When the vapor stream comes to the top of the reactive distillation column, it is condensed with the vapor mixture from an outlet O1 at the top of column by the condenser 4. The condensed stream is charged into the reflux drum 2 via an inlet I2 of the reflux drum and partially returns back via a reflux inlet R1 to provide a liquid stream, so the vapor phase and the liquid phase are in counter-current contact on the plates 111, 121 of the reactive distillation column, and the separation of the product from the reactant can be performed due to the difference between volatilities of components of the mixture. Finally, a bottom stream containing water, unreacted 1,4-butanediol and other heavy ends is given at the bottom outlet O3 of the reactive distillation column; and a top stream containing the product of tetrahydrofuran and water is discharged from a top outlet O2 of the reactive distillation column.

The method for producing THF of the present disclosure is capable of enhancing the operating stability and good heat transfer efficiency during the continuous process, by controlling the weight ratio of the water content of the bottom stream at the bottom outlet O3 to the water content of the top stream at the top outlet O2 within the range of from 0.05 to 2.4.

In a particular embodiment, the method for producing THF of the present disclosure further includes: feeding a reactant stream containing 1,4-butanediol into a reactive distillation apparatus comprising in turn from up and down a rectification section and a reactive section packed with acidic catalyst, and subjecting 1,4-butanediol to a dehydration reaction in the presence of the acidic catalyst to produce a top stream containing THF and a bottom stream from the reactive distillation apparatus, wherein the temperature of the reactive section is from 90 to 120° C., and the reactant stream containing 1,4-butanediol is controlled at a weight hourly space velocity of 2.1 to 2.5 $hr^{-1}$ so that the weight ratio of the water content in the bottom stream to the water content in the top stream is from 0.05 to 2.4, to solve the process problems due to the low conversion rate of the reaction and the settling of byproducts.

The present disclosure will be described in detail through Examples which are not considered to limit the scope of the present disclosure.

EXAMPLES

Example 1

The apparatus and arrangement systems shown in FIG. 1-3 were used. Firstly, a reactant stream containing 1,4-butanediol was fed through the inlet I1 into the reactive distillation column 1, wherein the reactant stream contains more than 99.98 wt % of 1,4-butanediol, and was fed at the first plate in the reactive section 12 of the reactive distillation column 1.

With the design of the plates 121 of the reactive section 12, the reactant 1,4-butanediol flowed into the catalyst packing zone 121b of the reactive section 12 and was subjected to a dehydration process in the presence of an acidic catalyst, wherein the acidic catalyst was an ion-exchange resin (Amberlyst-35 wet Type, Dow Chemical); the ion-exchange resin in an aqueous state had a total concentration of acid sites of 1.9 eq/L, a specific surface area of 50 $m^2/g$ and an average pore size of 30 nm.

Additionally, in Example the plate number of the rectification section of the reactive distillation column was 10, the plate number of the reactive section was 50, and the reaction conditions include: the weight hourly space velocity (WHSV) of 2.47 $hr^{-1}$, the temperature of the reactive section of from 105 to 120° C., the pressure of the reactive section of from 0.8 to 1.0 $kg/cm^2G$, and the temperature of the rectification section of from 96 to 100.8° C.

After being subjected to dehydration gradually in the catalyst packing zone 121b of each of the plates 121 in the reactive section, following by mass transfer and heat transfer in the distillation zone 121a and the rectification section, the reactant stream was heated at the bottom of the reactive distillation column through a reboiler 3. Therefore, the liquid stream at the bottom vaporized, and returned back to provide a vapor stream, wherein the temperature of the reboiler was 130° C.

After gradual purification, the vapor stream from an outlet O1 at the top of the reactive distillation column was condensed through a condenser 4, and was charged into a reflux drum 2 via an inlet I2 of the reflux drum, and a part was returned via the reflux inlet R1 to provide a liquid flow. As such, a gas stream and a liquid stream were in counter-current contact on the plates of the reactive distillation column.

Finally, a product, THF, was obtained from the top outlet O2.

By adjusting rates of materials discharged from the bottom outlet O3 and the top outlet O2 as well as the reflux ratio, the weight ratio of the water content of the bottom stream at the bottom outlet O3 to the water content of the top stream discharged from the top outlet O2 was controlled at 0.05. The results of conversion rates are recorded in Table 1.

Examples 2-8

The same production method was performed as in Example 1 to obtain THF, except that the weight ratio of the water content of the bottom stream to the water content of the top stream, the temperature of the reactive section, the weight hourly space velocity (WHSV), the temperature of the rectification section and the temperature of the reboiler were altered as shown in Table 1. The results of conversion rates are recorded in Table 1.

TABLE 1

|  |  |  | Ex. 1 | Ex. 2 | Ex. 3 | Ex. 4 |
|---|---|---|---|---|---|---|
| Ratio of water content at O3/water content at O2 |  |  | 0.05 | 0.08 | 0.16 | 0.5 |
| I1 Feeding rate (MT/hr) |  |  | 17 | | | |
| O2 | Discharging rate (MT/hr) |  | 16.3 | 16.2 | 16 | 15.3 |
|  | Composition | THF (wt %) | 80.5 | 81.0 | 82.0 | 85.3 |
|  |  | Water (wt %) | 19.5 | 19.0 | 18.0 | 14.7 |
| R1 reflux ratio |  |  | 0.19 | 0.195 | 0.23 | 0.4 |
| O3 | Discharging rate (MT/hr) |  | 0.7 | 0.9 | 1 | 1.74 |
|  | Composition | Water (wt %) | 22.8 | 31.0 | 43.8 | 62.3 |
|  |  | BDO (wt %) | 3.4 | 3.1 | 2.9 | 3.3 |
|  |  | Heavy Ends (wt %) | 73.8 | 65.9 | 53.3 | 34.4 |
| State of reactive distillation column |  |  |  |  |  |  |
| Reactive section | Temperature (° C.) |  | 105-120 | | | |
|  | Pressure (kg/cm²G) |  | 0.8-1.0 | | | |
|  | WHSV (hr⁻¹) |  | 2.47 | 2.43 | 2.39 | 2.34 |
|  | Water content (wt %) | Feed plate | 8.34 | 8.29 | 8.67 | 10.65 |
|  |  | lowermost plate | 93.1 | 93.1 | 93.1 | 92.86 |
| Rectification section Temperature (° C.) |  |  | 96-100.8 | 96.1-100.6 | 95-100 | 91.5-100.1 |
| Reboiler Temperature (° C.) |  |  | 130 | 127.1 | 122.8 | 119.9 |
| Steam consumption rate (MT/hr) |  |  | 8.2 | 8.1 | 8 | 7.9 |
| Liquid viscosity at the bottom (cp) |  |  | 0.513 | 0.423 | 0.345 | 0.325 |
| Reaction results |  |  |  |  |  |  |
| Conversion Rate (%) |  |  | 99.85 | 99.85 | 99.82 | 99.66 |

|  |  |  | Ex. 5 | Ex. 6 | Ex. 7 | Ex. 8 |
|---|---|---|---|---|---|---|
| Ratio of water content at O3/water content at O2 |  |  | 0.9 | 1.3 | 1.9 | 2.4 |
| I1 Feeding rate (MT/hr) |  |  | 17 | | | |
| O2 | Discharging rate (MT/hr) |  | 14.8 | 14.4 | 13.8 | 11.4 |
|  | Composition | THF (wt %) | 88.1 | 89.9 | 91.9 | 92.9 |
|  |  | Water (wt %) | 11.9 | 10.1 | 8.1 | 7.1 |
| R1 reflux ratio |  |  | 0.6 | 0.65 | 0.7 | 1 |
| O3 | Discharging rate (MT/hr) |  | 2.2 | 2.6 | 3.2 | 5.6 |
|  | Composition | Water (wt %) | 70.2 | 71.8 | 66.8 | 34.5 |
|  |  | BDO (wt %) | 2.6 | 3.4 | 10.1 | 48.4 |
|  |  | Heavy Ends (wt %) | 27.2 | 24.8 | 23.0 | 17.0 |
| State of reactive distillation column |  |  |  |  |  |  |
| Reactive section | Temperature (° C.) |  | 104-119 | | | 93-119 |
|  | Pressure (kg/cm²G) |  | 0.8-1.0 | | | |
|  | WHSV (hr⁻¹) |  | 2.27 | 2.16 | 2.15 | 2.13 |
|  | Water content (wt %) | Feed plate | 12.81 | 12.17 | 10.9 | 1.63 |
|  |  | lowermost plate | 93.23 | 92.53 | 89.1 | 67.46 |
| Rectification section Temperature (° C.) |  |  | 87.7-100.4 | 84.7-99.4 | 80.5-97.9 | 79.7-81.4 |
| Reboiler Temperature (° C.) |  |  | 119.5 | 119.4 | 119.7 | 123.6 |
| Steam consumption rate (MT/hr) |  |  | 8 | 7.6 | 7 | 6.6 |
| Liquid viscosity at the bottom (cp) |  |  | 0.27 | 0.267 | 0.279 | 0.429 |
| Reaction results |  |  |  |  |  |  |
| Conversion Rate (%) |  |  | 99.66 | 99.48 | 98.1 | 84 |

Comparative Examples 1-2

The same production method was performed as in Example 1 to obtain THF except that the weight ratio of the water content of the bottom stream to the water content of the top stream, the temperature of the reactive section, the weight hourly space velocity (WHSV), the temperature of the rectification section and the temperature of the reboiler were altered as shown in Table 2. The results of conversion rates were recorded in Table 2.

TABLE 2

|  |  |  | COM. EX. 1 | COM. EX. 2 |
|---|---|---|---|---|
| Ratio of water content at O3/water content at O2 |  |  | 0.04 | 2.42 |
| I1 | Feeding rate (MT/hr) |  | 17 | |
| O2 | Discharging rate (MT/hr) |  | 16.1 | 10.7 |
|  | Composition | THF (wt %) | 80.3 | 92.9 |
|  |  | Water (wt %) | 19.7 | 7.1 |
| R1 reflux ratio |  |  | 0.13 | 1.2 |
| O3 | Discharging rate (MT/hr) |  | 0.9 | 6.3 |
|  | Composition | Water (wt %) | 14.2 | 28.9 |
|  |  | BDO (wt %) | 18.0 | 55.4 |
|  |  | Heavy Ends (wt %) | 67.8 | 15.6 |
| State of reactive distillation column |  |  |  |  |
| Reactive section | Temperature (° C.) |  | 108-119 | 92-119 |
|  | Pressure (kg/cm²G) |  | 0.8-1.0 | |
|  | WHSV (hr⁻¹) |  | 3.09 | 2.00 |
|  | Water content (wt %) | Feed plate | 6.58 | 1.5 |
|  |  | lowermost plate | 88.89 | 62.9 |
| Rectification section Temperature (° C.) |  |  | 96.6-100.1 | 79.7-81.6 |
| Reboiler Temperature (° C.) |  |  | 143 | 124.9 |
| Steam consumption rate (MT/hr) |  |  | 7.8 | 7 |
| Liquid viscosity at the bottom (cp) |  |  | 0.67 | 0.485 |
| Reaction results |  |  |  |  |
| Conversion Rate (%) |  |  | 99.58 | 79.39 |

As seen from Tables 1 and 2, in Comparative Example 1, since the ratio of the water content of the bottom stream to the water content of the top stream was excessively low, the liquid viscosity at the bottom of the reactive distillation apparatus was raised to 0.67. Thus, in order to maintain a comparable extent of reaction, an increase in the temperature of the reboiler to supply a sufficient vapor stream is needed. As such, when an operation is carried for a long term, not only the process cost was increased, but also the problem that the acidic catalyst near the bottom of column tends to degradation occurred.

In Comparative Example 2, since the reflux ratio at the top of the reactive distillation apparatus was excessively high, the water content in the reactive section was excessively high, which was unfavorable to progress of the dehydration reaction. Therefore, the conversion rate of the reaction reduced greatly.

In conclusion, by employing the production method of the present disclosure, the reaction zone of the reactive distillation apparatus is maintained under a preferable reaction conversion conditions to significantly enhance the conversion rate of the reactant stream and to reduce equipment cost, by controlling the ratio of the water content in the bottom stream to that in the top stream, so that the process for producing THF has more economic benefits and values for industrial applications.

The above Examples are used for illustration only but not for limiting the present disclosure. Modifications and alternations can be made to above Examples by any one skilled in the art without departing from the spirit and scope of the present disclosure. Therefore, the range claimed by the present disclosure should be defined by the appended claims, and should be encompassed within the disclosure of the present disclosure as long as that doesn't influence effects and purposes of the present disclosure.

What is claimed is:

1. A method for producing tetrahydrofuran, comprising: feeding a reactant stream containing 1,4-butanediol into a reactive distillation apparatus, and performing a dehydration reaction in a presence of an acidic catalyst to produce a top stream containing tetrahydrofuran and a bottom stream from the reactive distillation apparatus, wherein a weight ratio of a water content in the bottom stream to a water content in the top stream is from 0.05 to 2.4.

2. The method of claim 1, wherein the reactive distillation apparatus comprises, from top to bottom, a rectification section and a reactive section, and wherein the reactive section is packed with the acidic catalyst.

3. The method of claim 1, wherein the reactant stream containing 1,4-butanediol has a weight hourly space velocity (WHSV) of from 2.1 to 2.5 hr⁻¹.

4. The method of claim 2, wherein the rectification section has 10 to 20 plates, and the reactive section has 40 to 60 plates.

5. The method of claim 4, wherein the reactant stream containing 1,4-butanediol is fed into the uppermost plate in the reactive section.

6. The method of claim 5, wherein a water content at the uppermost plate in the reactive section is from 1.6 to 13 wt %, and a water content at the lowermost plate in the reactive section is from 67 to 94 wt %.

7. The method of claim 2, wherein the rectification section is at a temperature of from 79 to 101° C.

8. The method of claim 2, wherein the reactive section is at a temperature of from 90 to 120° C.

9. The method of claim 1, wherein the bottom of the reactive distillation apparatus is connected to a reboiler, and a portion of the reactant stream is vaporized to a vapor stream in counter-current contact with the reactant stream containing 1,4-butanediol falling down in a liquid state along the reactive distillation apparatus.

10. The method of claim 2, wherein the reactive section is at a pressure of from 0.8 to 1.0 kg/cm$^2$G.

11. The method of claim 1, wherein the acidic catalyst is an acidic solid catalyst.

12. The method of claim 11, wherein the reactive section comprises a plurality of plates, and a plurality of catalyst packing zones for packing the acidic solid catalyst are arranged in each of the plurality of plates.

13. The method of claim 12, wherein the acidic solid catalyst is an ion-exchange resin.

14. The method of claim 13, wherein the ion-exchange resin in an aqueous state has a total concentration of acid sites of from 1.3 to 2.0 equivalents/liter.

15. The method of claim 13, wherein the ion-exchange resin has a specific surface area of from 20 to 50 m$^2$/g.

16. The method of claim 13, wherein the ion-exchange resin has an average pore size of from 30 to 70 nm.

17. The method of claim 13, wherein the reactant stream containing 1,4-butanediol has a weight hourly space velocity (WHSV) of from 2.1 to 2.5 hr$^{-1}$.

18. The method of claim 1, wherein a reflux ratio at the top of the reactive distillation apparatus is from 0.1 to 1.0.

19. The method of claim 1, wherein a liquid viscosity at the bottom of the reactive distillation apparatus is less than 0.6 centipoises (cps).

20. A method for producing tetrahydrofuran, comprising:
feeding a reactant stream containing 1,4-butanediol into a reactive distillation apparatus comprising, from top to bottom, a rectification section and a reactive section packed with an acidic catalyst; and
subjecting 1,4-butanediol to a dehydration reaction, in a presence of the acidic catalyst, to produce a top stream containing tetrahydrofuran and a bottom stream from the reactive distillation apparatus,
wherein the reactive section is at a temperature of from 90 to 120° C., and the reactant stream containing 1,4-butanediol is controlled at a weight hourly space velocity (WHSV) of from 2.1 to 2.5 hr$^{-1}$, and wherein a weight ratio of a water content in the bottom stream to a water content in the top stream is from 0.05 to 2.4.

* * * * *